United States Patent [19]

Mischenko

[11] Patent Number: 5,425,371
[45] Date of Patent: Jun. 20, 1995

[54] FIBEROPTIC PRESSURE TRANSDUCER

[75] Inventor: Peter S. Mischenko, Mount Prospect, Ill.

[73] Assignee: Metatech Corporation, Wheeling, Ill.

[21] Appl. No.: 144,897

[22] Filed: Oct. 28, 1993

Related U.S. Application Data

[63] Continuation of Ser. No. 956,638, Oct. 5, 1992, abandoned.

[51] Int. Cl.$^6$ .................................. A61B 5/0215
[52] U.S. Cl. .................................. 128/667; 128/675; 128/748; 73/705
[58] Field of Search ..................... 128/633–634, 128/664–667, 672–675, 748; 73/705, 708, 715

[56] References Cited

U.S. PATENT DOCUMENTS

| | | | |
|---|---|---|---|
| 4,611,600 | 9/1986 | Cohen | 128/687 |
| 4,691,708 | 9/1987 | Kane | 128/675 X |
| 4,787,396 | 11/1988 | Pidorenko | 128/675 X |
| 4,805,630 | 2/1989 | Storey | 128/675 |
| 4,924,877 | 5/1990 | Brooks | 128/667 X |
| 4,991,590 | 2/1991 | Shi | 128/675 X |
| 5,018,529 | 5/1991 | Tenerz et al. | 128/675 X |
| 5,065,010 | 11/1991 | Knute | 128/667 X |
| 5,195,375 | 3/1993 | Tenerz et al. | 128/675 X |

Primary Examiner—Angela D. Sykes
Attorney, Agent, or Firm—Jones, Day, Reavis & Pogue

[57] ABSTRACT

A fiberoptic fluid pressure transducer system involving a thin flat diaphragm, fiberoptic elements, a tubular member having an opening of fixed dimensions on the side thereof, an L-shaped cantilevered beam and a remotely located electronic control unit. The cantilevered beam has one leg horizontally attached to a recessed ledge surrounding the opening such that a vertical leg extending from the horizontal leg, including a light reflector, extends into the opening. A diaphragm covers the opening and makes physical contact with the horizontal leg of the L-shaped beam. Pressure applied to the diaphragm flexes the horizontal leg of the beam which, in turn, causes a spatial displacement of the vertical leg with respect to the fiberoptic elements. The resulting change in reception of the reflected light is proportional to the pressure applied to the diaphragm or membrane. The sensitivity of the transducer can be altered and the system can have two or more levels of sensitivity over a range of pressure measurements.

4 Claims, 2 Drawing Sheets

FIBEROPTIC PRESSURE TRANSDUCER

This is a continuation of application Ser. No. 07/956,638 filed on Oct. 5, 1992, now abandoned.

FIELD OF THE INVENTION

The present invention relates to a pressure transducer in general and in particular to a fiberoptic pressure transducer that can be mounted in the end of a tubular rod and that changes the amount of reflected light received by a fiberoptic rod in proportion to an applied pressure.

BACKGROUND OF THE INVENTION

The basic principle of fiberoptic transducers revolves around shining a light on a reflective surface and measuring how much light is reflected back to a fiberoptic rod. The amount of light that is reflected is determined by the distance that the reflective surface is located from the light source and light collector. In general, fiberoptic transducers use one or more fibers to channel light from the light source to a reflective surface and use one or more fiberoptic rods to collect the reflected light from the reflective surface and channel it to a measuring device.

In the prior art, one type of pressure measuring device, as disclosed in U.S. Pat. No. 4,787,396, uses a diaphragm that is reflective or has reflective elements attached to it. As the pressure moves the diaphragm, the reflecting surface is moved towards or away from the light transmitting rods or optical fibers to change the amount of reflected light in proportion to the pressure applied to the diaphragm. Generally, the sensitivity of a pressure transducer is governed by the flexibility of the diaphragm, by its thickness by and its surface area. For medical applications, it is desirable to make the transducers as small as possible. As the diameter of the diaphragm decreases, the sensitivity of the diaphragm to pressure decreases in a way that is inversely proportional to the square of the diameter. This can be partially offset by decreasing the thickness of the diaphragm. There are limits, however. The first limitation is a physical limitation in making progressively thinner diaphragms without making them porous. The other limitation is the cost of economically forming very thin diaphragms.

To attempt to overcome these disadvantages, transducers such as those disclosed in U.S. Pat. No. 5,065,010 were developed. In this patent, the diaphragm is a miniature bellows which can be altered in its length, number of convolutions and the material thickness to vary its sensitivity. The major disadvantage of this particular pressure transducer is that a cavity is created in which fluid is collected. In the case where the fluid is blood, it tends to coagulate in this cavity. This eventually leads to error in reading the correct average pressure as well as a deterioration of the frequency response of the transducer. This damping or degradation of the measured pressure wave form may cause misdiagnosis of a patient's true medical condition.

Another limitation of prior art pressure transducers involves the end use of the transducer. If a transducer having a diaphragm is inserted in a blood vessel or other fluid conduit, there is an inherent error in measuring the correct pressure due to errors introduced by the flow of fluid impinging normal to the diaphragm. The static pressure is increased by the dynamic pressure of the flowing fluid against the diaphragm.

A further improvement was disclosed in U.S. Pat. No. 4,991,590 in which a cylindrically shaped pressure sensor has a side window and an L-shaped thin leaf having two sections including a reflector section arranged at an angle of approximately 90° to the other section, the other section being movably situated within the side window with one end of the reflector section being attached to the outer cylinder wall opposite to the window. A membrane surrounds the cylinder to seal the pressure sensing mechanism from fluid and to permit the transmission of pressure to the L-shaped leaf. One of the disadvantages with this transducer is that the leg of the L-shaped leaf containing the reflector portion is cemented or otherwise affixed in a slit in the housing wall opposite the side window. This requires a bending moment about the base of the leg that contains the reflective element. Since the L-shaped leaf is made of a flexible material, the bending moment of the leg containing the reflective element may cause the reflective element itself to bend, thus causing a nonlinearity in the reading taken. Further, the sensitivity of the instrument is not easily adjusted since the thin leaf has a long horizontal leg to provide enough bending moment to flex the vertical leg that has the reflective element and that is attached at the end thereof to the side wall.

The present invention overcomes the disadvantages of the prior art by providing a pressure transducer that consists of a tubular member in which an opening or cavity is provided in the side of the tubular member. An L-shaped beam has one leg attached horizontally to the tubular member in a cantilever fashion such that the other leg extends vertically into the cavity. A reflective surface is formed on at least one side of the vertically extending leg and a flexible membrane covers the cavity and is in contact with the horizontal leg of the L-shaped beam. At least one fiberoptic rod is mounted in the housing in spaced relationship with the vertical leg for transmitting light to and receiving light from the reflective surface such that when pressure is applied to the membrane, the horizontal leg is flexed inwardly thus changing the angular position of the vertical leg with respect to the fiberoptic rod, thereby changing the amount of reflected light in an amount proportional to the applied pressure. A recessed ledge is formed around the opening or cavity in the housing for receiving the horizontal leg of the L-shaped leaf and the flexible diaphragm that covers the cavity or opening. With a slot in the horizontal leg of the L-shaped leaf and an orifice in the recessed ledge around the cavity or opening for receiving an attachment device through the slot in the horizontal leg of the leaf, more or less of the horizontal leg may be caused to extend over the edge of the recessed ledge a distance L1. By adjusting the length L1 of the horizontal leg in relation to the length of the vertical leg, L2, the sensitivity of the probe or transducer may be varied or altered. This occurs because there is a geometric relationship between the distances L1 and L2 which affects the displacement of the reflecting surface in relation to the displacement of the end of the horizontal portion of the cantilevered beam caused by a pressure exerting a force on the horizontal beam. Thus, the displacement of the outer end of the horizontal leg can be mechanically amplified or deamplified by choosing different ratios of L1:L2.

Further, with this design, the problem of fluid flow perpendicular to the diaphragm is avoided since the membrane is on the side of the tubular member and is essentially flat. Also, no stagnant area is present for fluid to gather or, in the case of blood, to coagulate. It also enables the transducer to be more easily configured to suit sensitivity requirements.

With the present invention, the L-shaped leaf can be mounted to the recessed ledge to establish a first pressure sensitivity over a first range of flexure of the horizontal leg and a second pressure sensitivity over a second range of flexure of the horizontal leg. This is accomplished by forming an angled portion on the outer end of the horizontal leg and attaching the outer end of the horizontal leg to the recessed ledge such that the remaining portion of the horizontal leg, in its normal position, is angled upwardly and does not touch the edge of the recessed ledge, whereby a first pressure deflects the angled portion of the horizontal leg until it contacts the edge of the recessed ledge. A second greater pressure further deflects the portion of the horizontal leg beyond and below the edge of the ledge, thus creating first and second pressure sensitivities of the transducer. The cantilevered beam is attached at a point on the recessed ledge of the tubular member such that the length L1 of the horizontal leg is the effective length of the horizontal leg and is slightly angled apart from the attaching ledge or attaching surface. As increasing pressure is applied, the horizontal leg deflects, causing the angle to decrease until the horizontal leg touches the edge of the recessed ledge. At this point, the effective length of the beam has been shortened to a length L3. With an effective length of L1, the transducer is more sensitive than when the effective length is L3. It is therefore possible to construct a transducer which is more accurate when measuring low pressures, such as intracranial and left atrial pressures, and less accurate when measuring higher pressures, such as arterial cardiovascular pressures. As an example, a one millimeter of mercury error when measuring 10 millimeters of intracranial pressure, a 10% error, is more significant than a 3 millimeter error in reading a cardiovascular pressure of 100 millimeters, a 3% error.

Thus, it is an object of the present invention to provide a fiberoptic pressure transducer that avoids error caused by fluid flow impinging normal to the diaphragm or membrane.

It is also an object of the present invention to provide a fiberoptic transducer that does not have an open cavity in which fluid may be collected and, in the case of blood, coagulated which leads to error in reading the correct average pressure as well as causing deterioration of the frequency response of the transducer.

It is yet another object of the present invention to provide a pressure transducer in which the sensitivity of the transducer is tailored to the application.

It is still another object of the present invention to provide a pressure transducer in which two or more levels of sensitivities for two or more ranges of pressure may be provided simultaneously.

It is yet another object of the present invention to provide a pressure transducer in which an L-shaped beam has one leg attached horizontally to a tubular member in cantilevered fashion such that the other leg extends vertically into a cavity in the tubular member, the vertical leg having a reflective surface thereon. A flexible membrane covers the cavity and is in contact with the horizontal leg of the L-shaped beam. At least one fiberoptic rod is mounted in the housing in spaced relationship with the vertical leg for transmitting light to and receiving light from the reflective surface such that pressure applied to the membrane flexes the horizontal leg inwardly to change the angular position of the vertical leg with respect to the fiberoptic rod and change the amount of received reflected light proportional to the applied pressure.

SUMMARY OF THE INVENTION

Thus the present invention relates to a fiberoptic pressure transducer comprising a tubular member having a cavity in the side thereof, an L-shaped beam having one leg attached horizontally to the tubular member in cantilevered fashion such that the other leg extends vertically into the cavity, a reflective surface on at least one side of the vertically extending leg, a flexible membrane covering the cavity and in contact with the horizontal leg of the L-shaped beam, and at least one fiberoptic rod mounted in the housing in spaced relationship with the vertical leg for transmitting light to and receiving light from the reflective surface such that the pressure applied to the membrane flexes the horizontal leg inwardly to change the spatial position of the vertical leg with respect to the fiberoptic rod and change the amount of reflected light proportional to the applied pressure.

BRIEF DESCRIPTION OF THE DRAWINGS

These and other objects of the present invention will be more fully disclosed when taken in conjunction with the attached detailed description of the drawings in which like numerals represent like elements and in which.

DETAILED DESCRIPTION OF THE DRAWINGS

Figure 1:
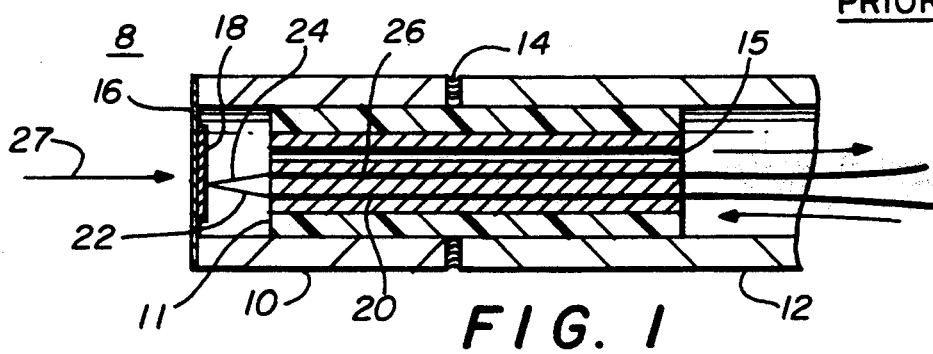
FIG. 1 is a first embodiment of a prior art fiberoptic pressure transducer.

A prior art transducer of the type described in U.S. Pat. No. 4,787,396, incorporated herein by reference, is disclosed schematically in FIG. 1. The pressure transducer 8 of FIG. 1 is a stainless steel tip suitable for use in catheter applications. The tip includes hollow cylindrical cap 10, ferrule 11 and flexible diaphragm 16 which has a light reflecting surface 18 on the inside thereof that reflects light rays 22 that exit from the end of optical fiber 20 and, depending upon the angle of reflection, either pass back into fiber 26 along path 24 or are reflected outside the end of fiber 26. It is to be understood that only one fiber optical rod may be utilized as described in U.S. Pat. No. 4,787,396. Ferrule 11 is also inserted in hollow body portion 12 of the catheter, and cap 10 and body portion 12 are joined thereto at 14 in any well-known means to form a single unit. A passageway 15 provides a vent opening for communication to atmospheric pressure and for calibrating the transducer. The pressure may be established at a desired value for calibration purposes. The operation of this pressure transducer is disclosed in detail in U.S. Pat. No. 4,787,396 and will not be repeated here. One of the problems with this type of transducer occurs when the catheter is inserted in a blood vessel or other fluid conduit. There is an inherent error in measuring the correct pressure due to errors introduced by the flow of fluid 27 impinging on the diaphragm 16 in a plane normal to the plane of the diaphragm 16 because the force of the flow adds to the normal static pressure.

Figure 2:
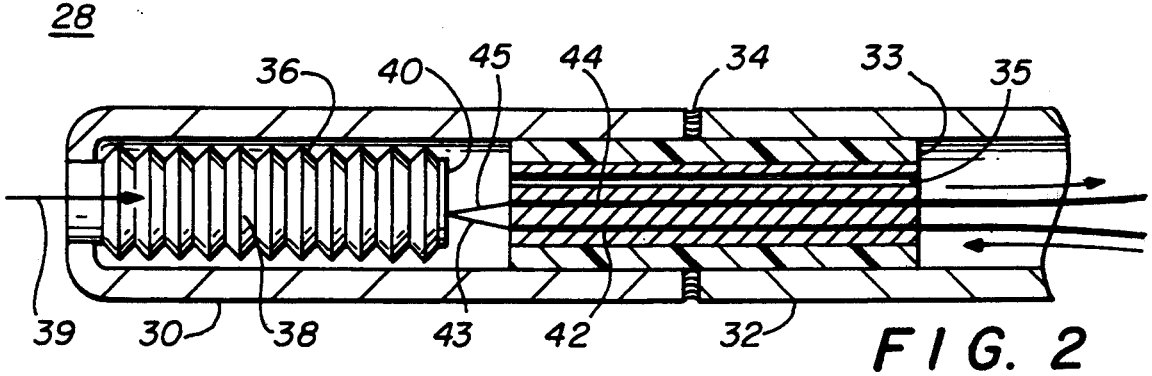
FIG. 2 is a second embodiment of a prior art pressure transducer.

FIG. 2 illustrates a second pressure transducer generally of the type disclosed in U.S. Pat. No. 5,065,010 also incorporated herein by reference in its entirety. In FIG. 2, the pressure transducer 28 includes a tip 30 attached to catheter tube 32 at joinder 34 in any well-known manner. Ferrule 33 is inserted in both the tip 30 and the catheter tube 32 and is stationarily affixed to tube 32. A bellows-type diaphragm 36 is located in the tip 30 and forms a cavity 38 in which the flow 39 can enter and impinge upon the back side of the reflecting surface 40. A source fiberoptic rod 42 is used to emit light 43 in the direction of the reflective surface 40 coupled to the diaphragm 36 for reflection to the signal optical fiber 44 along path 45. Because the reflective surface 40 is a flat surface, a reflected beam is formed. In response to pressure caused by flow 39, the reflective surface 40 moves toward and away from the fiberoptic rods 42 and 44. The signal fiber 44 is located so as to be relatively sensitive to the reflected beam intensity changes. The intensity of the received light is therefore proportional to the applied pressure. Passageway 35 through ferrule 33 enables communication to atmospheric pressure. The major problem with this particular design is that the cavity 38 is created in which fluid is collected. In the case of a fluid such as blood, the fluid tends to coagulate in this cavity. This eventually leads to error in reading the correct average pressure and also causes deterioration of frequency response of the transducer. This damping or degradation of the measured pressure wave form may cause misdiagnosis of a patient's true medical condition. Further, the flow again impinges upon the back side of the reflective surface 40 in a plane normal to the plane of the reflective surface 40. This creates a problem in regard to inherent pressure measurement error discussed earlier in relation to FIG. 1.

Figure 3:
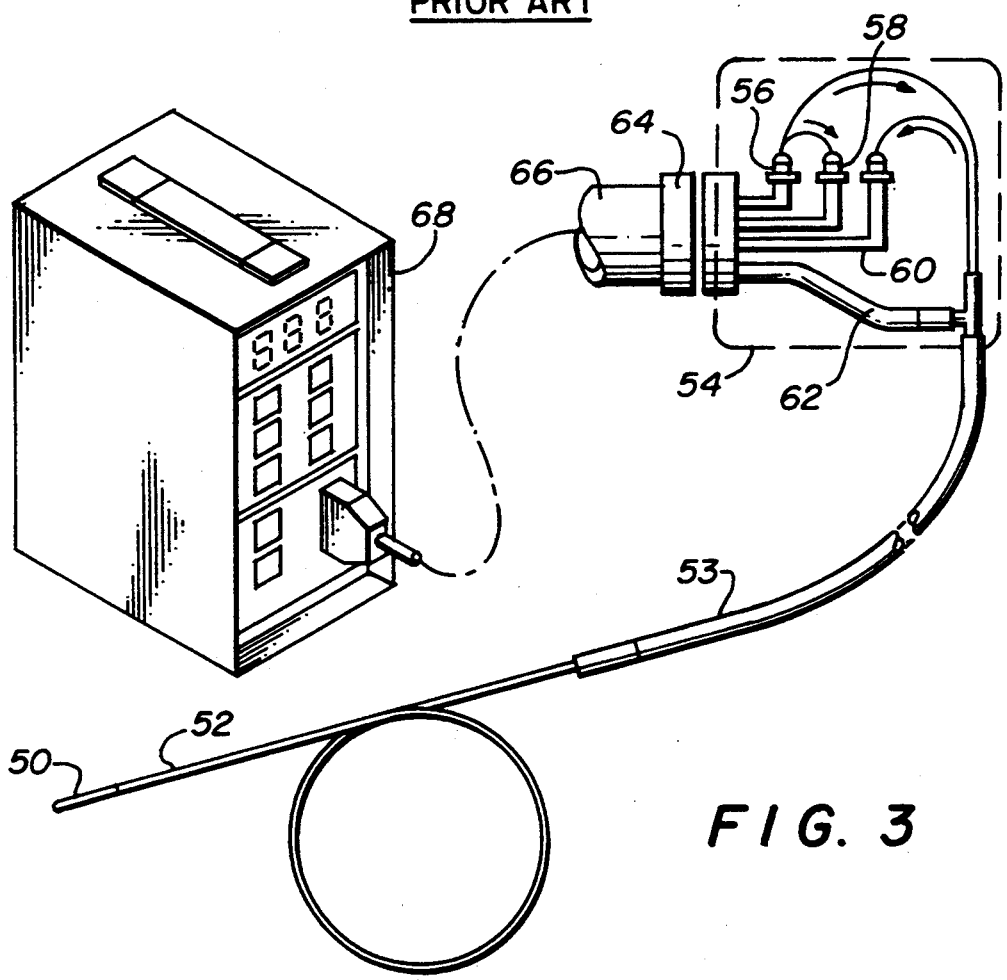
FIG. 3 is a diagrammatic representation of the system of the present invention utilizing the novel fiberoptic pressure transducer disclosed herein.

The system of the present invention is illustrated in FIG. 3 and includes a pressure tip 50 joined to a catheter 52. The catheter 52 is coupled by a housing or tube 53 to a light coupling device 54. Device 54 includes a light source 56, a reference photo detector 58 and a reflected light return photo detector 60. A conduit 62 is utilized for communicating to atmospheric pressure and for calibration of the device. The electrical signals from device 54 are coupled through coupler 64 and conduit 66 to a control unit 68 where they are converted to a readout display developed either in analogue or digital form. The system is basically well known and will not be described in detail here.

Figure 4:
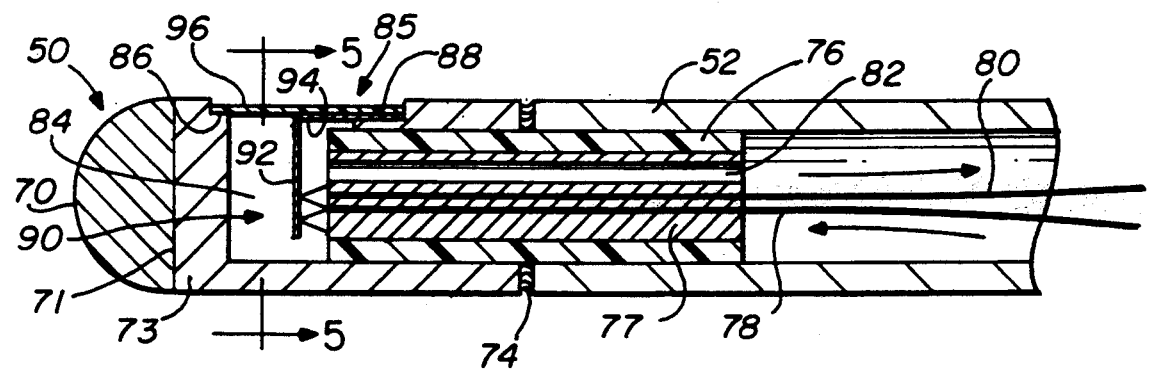
FIG. 4 is a diagrammatic representation of a cross-sectional view of the novel transducer disclosed herein.

The novel pressure transducer tip 50 is disclosed in diagrammatic form as a partial cross section in FIG. 4. The tip 50 is joined to the catheter tube 52 at 74 in any well-known manner. End cap 70 is attached to stainless steel tube 73 in any well-known manner. A stainless steel support 76 is inserted in and joined to both the tube 73 and the catheter tube 52. The support 76 encloses an epoxy 77 that supports the fiberoptic rods 78 and 80 and has a passageway 82 therein for equalizing the pressure on both sides of support 76. A cavity 84 having an external opening 85 is formed in the side of the tube 73. A recessed ledge is formed around the opening 85, as can be more clearly seen in FIG. 6, and has a narrow ledge 86 on one end and a larger ledge 88 on the other end. A flexible L-shaped leaf 90 formed of stainless steel having a preferred thickness of 0.001 inch and a preferred width of 0.014 inch has one leg 94 attached horizontally at one end in a cantilevered fashion to the ledge 88 to allow the other leg 92 to extend vertically into the cavity 84. A thin, flexible diaphragm or membrane 96 covers the opening 85 of cavity 84 and contacts the horizontal leg 94 of the cantilevered L-shaped leaf 90. The membrane 96 may be of any material impervious to moisture penetration and with the same temperature expansion of steel tube 73. In a most preferred embodiment, the membrane is 60 millionths of an inch thick and is formed from a cobalt super alloy such as products with the trade names of HAVAR and ELGILOY. Because the membrane 96 is flexible, a change in pressure of the fluid in which the catheter 52 is inserted forces the membrane 96 inwardly against horizontal leg 94 of the L-shaped leaf 90 and forces leaf 90 inwardly. A reflective surface is formed on one side of the vertical leg 92 of the L-shaped leaf 90 that extends into the cavity 84. The reflective surface is in spaced relationship with the ends of the fiberoptic rods 78 and 80 mounted in tube 76. Fiberoptic rod 78 transmits light to the reflective surface on vertical leg 92 of leaf 90 and fiberoptic rod 80 receives light from the reflective surface on the vertical leg 92. When pressure is applied to the diaphragm 96, the horizontal leg 94 of leaf 90 is depressed or flexed inwardly, thus causing the vertical leg 92 of the leaf structure 90 to move toward tube 76 thus changing the spatial position of the reflective surface on vertical leg 92 with respect to the fiberoptic rods 78 and 80 so as to change the amount of reflected light received by the fiberoptic rod 80 in proportion to the applied pressure.

The sensitivity of this type of construction can be easily altered in several manners. One method of changing sensitivity is to change the effective area of the diaphragm 96 by changing the dimensions of the external opening 85 of cavity 84. The sensitivity may also be easily altered by changing the width and thickness of the horizontal leg 94 of the L-shaped leaf 90. This can be seen more clearly in FIG. 6 which is a top view of the pressure transducer tip 50 of FIG. 4.

Figure 5:
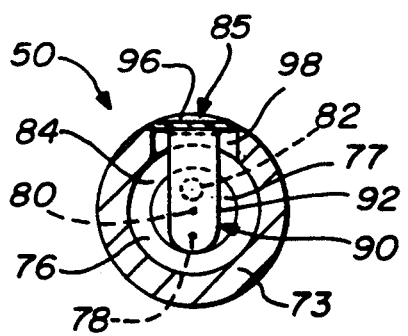
FIG. 5 is a cross-sectional view of the transducer shown in FIG. 4 taken along lines 5—5.

FIG. 5 is a cross-sectional view taken along lines 5—5 of FIG. 4 and illustrates the tip 50, the tube 76 and the ends of the fiberoptic rods 78 and 80. The vertical leg 92 of the L-shaped leaf 90 is illustrated in front of the ends of the fiberoptic rods 78 and 80. The diaphragm or membrane 96 can be seen on the recessed ledge that surrounds the external opening 85 of cavity 84.

Figure 6:
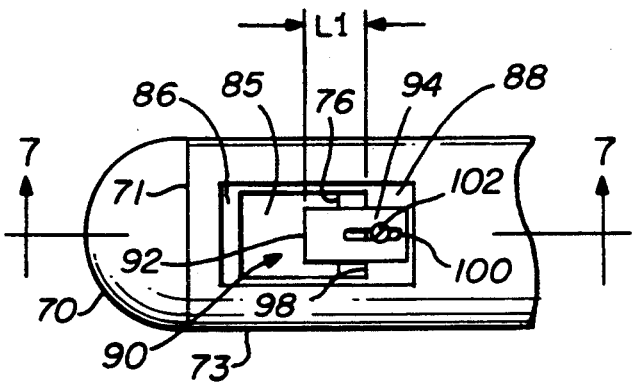
FIG. 6 is a top view of the outer end of the pressure transducer illustrating the cavity in the tubular member, the recessed ledge around the cavity and the L-shaped cantilevered beam mounted on the recessed ledge by means of the horizontal leg and with the vertical leg extending into the cavity.
Figure 7:
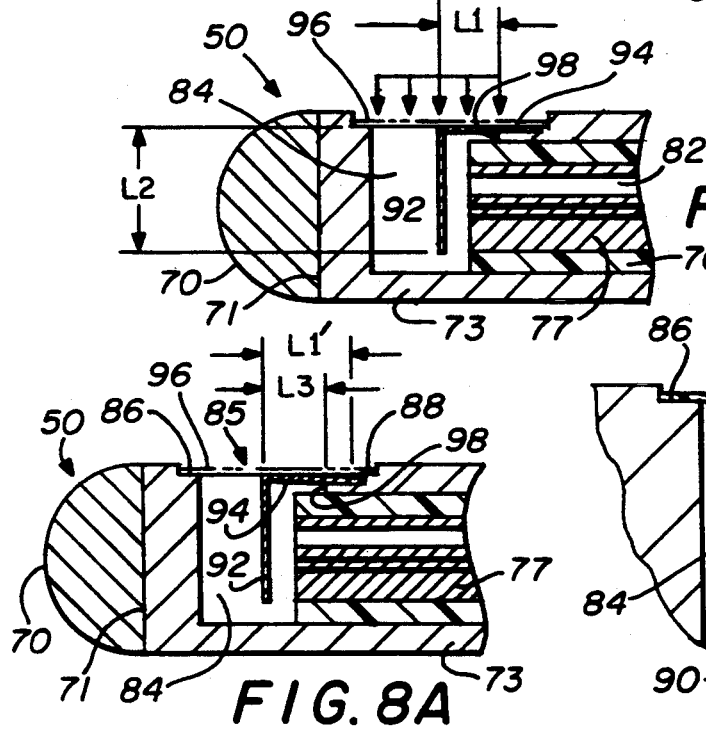
FIG. 7 is a cross-sectional side view of the outer end of the novel pressure transducer illustrating a first manner in which the pressure sensitivity can be varied.

FIG. 7 is a schematic side view of the tip 50 illustrating the manner in which the sensitivity of the transducer may be altered by the amount the horizontal leg 94 of the L-shaped leaf 90 extends beyond the edge 98 of ledge 88. Clearly, the more the horizontal leg 94 extends beyond the edge 98 of the ledge 88, the more flexibility it will have and the more sensitivity it will have. The more the membrane or diaphragm 96 moves inwardly, the greater the spatial movement of the vertical leg 92 with respect to the ends of the fiberoptic rods 78 and 80. To make this adjustment, a slot 100 may be formed in the horizontal leg 94 as illustrated in FIG. 6. A fastening device such as screw 102 may be inserted in the orifice and may be tightened or loosened to allow the horizontal leg 94 to be moved outwardly to a maximum length determined by the length of slot 100, the screw tightened and the sensitivity adjusted.

There is a geometric relationship between the distance, L1, the extent by which the horizontal leg 94 extends beyond the edge 98 of ledge 88 and the distance L2 which is the length of the vertical leg 92. This ratio affects the spatial displacement of the end of the vertical leg 92 with the reflecting surface thereon in relation to the displacement of the outer end of the cantilevered horizontal leg 94 by the inward pressure on the membrane 96. In other words, the displacement of the horizontal leg 94 by the pressure applied thereto can be mechanically amplified or deamplified by choosing different ratios of the lengths L1:L2.

The design of the present invention also addresses the problem of perpendicular fluid flow because the cavity is on the side of the probe 50 and, since the diaphragm or membrane 96 is essentially flat, no stagnant area is present for blood to coagulate. It also addresses the problem of being able to more easily create configurations to suit sensitivity requirements.

Figure 8A:
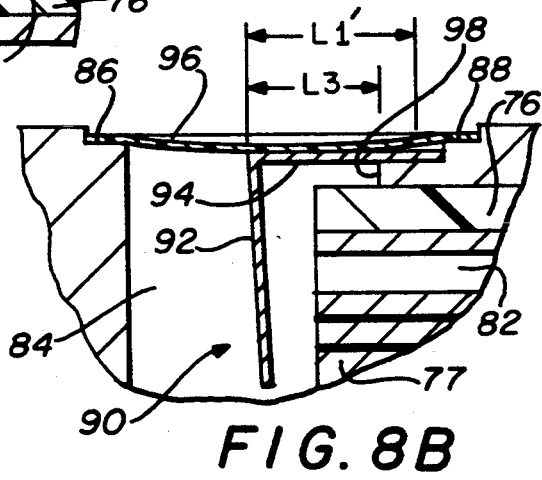
FIG. 8A is a schematic cross-sectional view of the novel pressure transducer illustrating a second embodiment for creating a first and second pressure sensitivity, the first pressure sensitivity being illustrated in FIG. 8A.
Figure 8B:
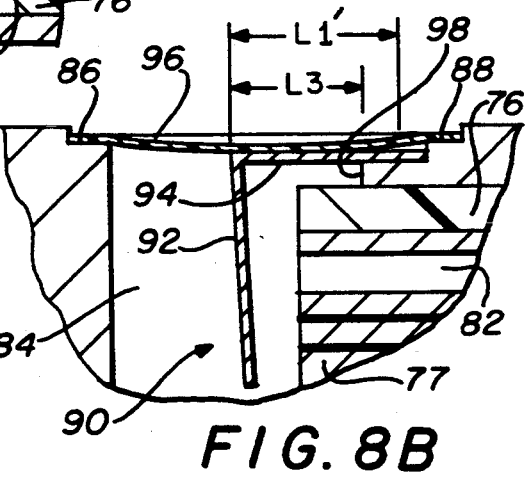
FIG. 8B is a schematic representation of the transducer of FIG. 8A in the second sensitivity position.

An additional configuration shown in FIG. 8A can be created to produce a transducer that has two or more levels of sensitivity over a range of pressures. As can be seen in FIG. 8A the cantilever beam horizontal leg 94 is attached to the recessed ledge 88 such that a portion L1' is slightly angled outwardly and upwardly from the attaching surface 88 and is the effective length of the horizontal leg 94. As increasing pressure is applied to the membrane 96, the portion L1' of beam 94 deflects causing the slight angulation of the portion L1' to decrease until it touches the edge 98 of the mounting recessed ledge 88 similar to that shown in FIG. 7. At this point the effective length of the beam becomes L3. With an effective length of L1' the transducer is more sensitive then when the effective length is L3. It is therefore possible to construct a transducer which is more accurate when measuring low pressures such as intracranial and left atrial pressures and less accurate when measuring higher pressures, such as arterial cardiovascular pressures. As an example, a 1 millimeter of mercury error when measuring ten millimeters of intracranial pressure is a 10 percent error and is more significant than a 3 millimeter error in reading a cardiovascular pressure of 100 millimeters which is a 3 percent error. FIG. 8B more clearly illustrates the distance L3 when the membrane 96 has forced the horizontal leg 94 from its angled position to a flat position where it touches the edge 98 of ledge 88.

Thus, there has been disclosed a novel fiberoptic pressure transducer that avoids the problem of perpendicular fluid flow because the cavity and covering membrane are on the side thereof. Further, since the diaphragm or membrane is essentially flat, there is no stagnant area present for blood to coagulate. Further, the novel cantilevered beam construction provides easily adjustable configurations to suit sensitivity requirements. The novel transducer can have two or more levels of sensitivity over a range of pressures. Further, the cantilevered beam is attached to the transducer by a horizontal leg of an L-shaped leaf being attached to the side or recessed ledge of the surrounding cavity. The vertical leg extends into the cavity. This construction allows the sensitivity adjustments to be made as explained previously.

The foregoing specification describes only the embodiments of the invention shown and/or described. Other embodiments may be articulated as well. The terms and expressions used, therefore, serve only to describe the invention by example and not to limit the invention. It is expected that others will perceive differences which, while different from the foregoing, do not depart from the scope of the invention herein described and claimed. In particular, any of the specific constructional elements described may be replaced by any other known element having equivalent function.

I claim:

1. A fiberoptic pressure transducer comprising:
   a housing with a side wall;
   an opening in the wall extending into a cavity formed in the housing;
   a flexible L-shaped leaf structure having two legs, one leg being attached at one end to the wall and extending horizontally in a cantilevered fashion for a length over said cavity with the other leg extending vertically into the cavity;
   a flexible diaphragm covering the opening and contacting the horizontal leg of the cantilevered L-shaped leaf structure;
   a reflective surface on one side of the vertical leg of the L-shaped leaf structure that extends into the cavity;
   at least one fiberoptic rod mounted in the housing in spaced relationship with the reflective surface for transmitting light to and receiving light from the reflective surface such that when pressure is applied to the diaphragm, the vertical leg of the leaf structure is flexed inwardly into said cavity in response to the applied pressure and the spatial position of the reflective surface changes with respect to the at least one fiberoptic rod so as to change the amount of reflected light received by the at least one fiberoptic rod in proportion to the applied pressure; and
   means for adjusting the length of the horizontal leg of the L-shaped leaf structure that extends over the cavity to vary sensitivity of the pressure transducer.

2. A fiberoptic pressure transducer comprising:
   a housing with a side wall;
   an opening in the wall extending into a cavity formed in the housing;
   a flexible L-shaped leaf structure having two legs, one leg being attached at one end to the wall and extending horizontally in a cantilevered fashion for a length over said cavity with the other leg extending vertically into the cavity;
   a flexible diaphragm covering the opening and contacting the horizontal leg of the cantilevered L-shaped leaf structure;

a reflective surface on one side of the vertical leg of the L-shaped leaf that extends into the opening; and at least one fiberoptic rod mounted in the housing in spaced relationship with the reflective surface for transmitting light to and receiving light from the reflective surface such that when pressure is applied to the diaphragm, the vertical leg of the leaf structure is flexed inwardly into said cavity in response to the applied pressure and changes the spatial position of the reflective surface changes with respect to the at least one fiberoptic rod so as to change the amount of reflected light received by the at least one fiberoptic rod in proportion to the applied pressure;

a recessed ledge around the opening in the housing wall for receiving the horizontal leg of the L-shaped leaf structure and the flexible diaphragm covering the opening; and a sensitivity adjusting means comprising:

a slot in the horizontal leg of the L-shaped leaf structure; and an orifice in the recessed ledge around the opening such that an attachment device removably inserted in the orifice through the slot allows the length of the horizontal leg extending over the cavity to be adjusted thus varying the flexibility and the pressure sensitivity of the transducer.

3. A pressure transducer as in claim 2 further including mounting means for attaching the L-shaped leaf to the recessed ledge so as to establish a first pressure sensitivity over a first range of flexure of the horizontal leg and a second pressure sensitivity over a second range of flexure of the horizontal leg.

4. A fiberoptic pressure transducer comprising:

a housing with a side wall;

an opening in the wall extending into a cavity formed in the housing;

a flexible L-shaped leaf structure having a first and a second leg, said first leg being attached at a first end to the wall and extending horizontally in a cantilevered fashion for a length over said cavity and being attached at a second end to the second leg, said second leg extending vertically into the cavity;

a flexible diaphragm covering the opening and contacting the horizontal leg of the cantilevered L-shaped leaf structure;

a reflective surface on one side of the vertical leg of the L-shaped leaf structure that extends into the cavity;

at least one fiberoptic rod mounted in the housing in spaced relationship with the reflective surface for transmitting light to and receiving light from the reflective surface such that when pressure is applied to the diaphragm the vertical leg of the leaf structure is flexed inwardly into said cavity in response to the applied pressure and the spacial position of the reflective surface changes with respect to the at least one fiberoptic rod so as to change the amount of reflected light received by the at least one fiberoptic rod in proportion to the applied pressure;.

a recessed ledge having a bearing surface extending in a horizontal plane and including an edge around the opening in the housing wall for receiving the horizontal leg of the L-shaped leaf structure and the flexible diaphragm covering the opening;

mounting means for attaching the L-shaped leaf structure to the recessed ledge so as to establish a first pressure sensitivity over a first range of flexure of the horizontal leg and a second pressure sensitivity over a second range of flexure of the horizontal leg;

the mounting means comprising:

an angled portion formed intermediate said first end and said second end end of the horizontal leg; and connecting means for attaching the first end of the horizontal leg to the recessed ledge such that the angled portion of the horizontal leg is angled upwardly relative to the horizontal plane of said bearing surface and does not touch the edge of the recessed ledge whereby a first pressure deflects the angled portion of the horizontal leg until it contacts the edge of the recessed ledge and a second greater pressure deflects the second end of the horizontal leg beyond the ledge below the plane of the bearing surface of the ledge.

* * * * *